(12) United States Patent
Eynard et al.

(10) Patent No.: US 7,872,146 B2
(45) Date of Patent: Jan. 18, 2011

(54) PROCESS FOR THE PREPARATION OF A CARBOXAMIDE DERIVATIVE

(75) Inventors: Thierry Eynard, Villars les Dombes (FR); Cécile Franc, Lyons (FR)

(73) Assignee: Bayer CropScience AG, Monheim (DE)

( * ) Notice: Subject to any disclaimer, the term of this patent is extended or adjusted under 35 U.S.C. 154(b) by 398 days.

(21) Appl. No.: 11/913,151

(22) PCT Filed: May 6, 2006

(86) PCT No.: PCT/EP2006/004566

§ 371 (c)(1),
(2), (4) Date: May 13, 2008

(87) PCT Pub. No.: WO2006/120031

PCT Pub. Date: Nov. 16, 2006

(65) Prior Publication Data

US 2009/0062552 A1  Mar. 5, 2009

(30) Foreign Application Priority Data

May 13, 2005  (EP)  ................................. 05356080

(51) Int. Cl.
*C07D 231/10*  (2006.01)

(52) U.S. Cl. ..................... 548/374.1; 548/127; 548/146; 548/206; 548/215; 548/400; 544/336; 549/13; 549/70; 549/356; 549/483

(58) Field of Classification Search ............... 548/374.1
See application file for complete search history.

(56) References Cited

FOREIGN PATENT DOCUMENTS

| EP | 0 824 099 | 11/2001 |
|----|-----------|---------|
| WO | WO 2004/007203 | 8/2004 |
| WO | WO 2004/103975 | 12/2004 |

*Primary Examiner*—Yong Chu
*Assistant Examiner*—Samantha L Shterengarts
(74) *Attorney, Agent, or Firm*—Baker Donelson Bearman, Caldwell & Berkowitz

(57) ABSTRACT

Process for the preparation of a carboxamide derivative of formula (I) or a salt thereof

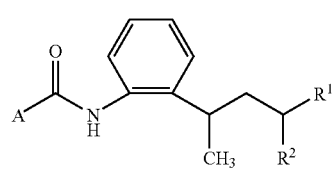

(I)

Intermediates for preparing this compound are also provided.

20 Claims, No Drawings

PROCESS FOR THE PREPARATION OF A CARBOXAMIDE DERIVATIVE

CROSS REFERENCE TO RELATED APPLICATIONS

This is a §371 National Stage Application of International Application No. PCT/EP2006/004566 filed May 6, 2006, which claims priority from European Application No. 05356080.1 filed May 13, 2005.

BACKGROUND OF THE INVENTION

1. Field of the Invention

The present invention relates to a novel process for the preparation of a carboxamide derivative which is useful as a pesticide compound, starting with a nitrobenzene derivative.

2. Description of Related Art

Patent application EP-A-0824099 discloses a process for the preparation of a carboxamide derivative starting from a nitrobenzene derivative. The process disclosed in this patent application presents the drawback in that the aromatic amine is prepared by reacting a nitro derivative with a Grignard reagent. This reaction yields to numerous by-products which decreases severely the reaction yield. This process can not be used at an industrial scale.

Furthermore, Journal of Organometallic Chemistry 2001, 624, pages 167-171 teaches that quenching the reaction with ammonia allows to increase the selectivity and thus, the reaction yield, but that such a process is not efficient when secondary magnesium halides are involved.

SUMMARY OF THE INVENTION

We have now found an alternative method to prepare carboxamide derivative from nitro compounds which overcomes these problems and which is applicable to industrial scale operation.

DETAILED DESCRIPTION OF A PREFERRED EMBODIMENT

Accordingly, the present invention relates to a process for the preparation of a carboxamide derivative of general formula (I) or a salt thereof

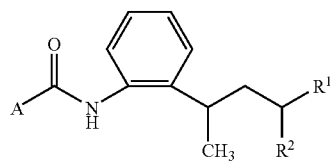

(I)

in which:
$R^1$ represents a methyl group, an ethyl group or a $C_1$-$C_4$-haloalkyl group substituted with 1 to 9 halogen atoms chosen from fluorine, chlorine and bromine;
$R^2$ represents a halogen atom, a $C_1$-$C_4$-alkyl group or a $C_1$-$C_4$-haloalkyl group substituted with 1 to 9 halogen atoms chosen from fluorine, chlorine and bromine; and
A represents an optionally substituted 5-, 6- or 7-membered non-fused heterocycle with one, two or three heteroatoms which may be the same or different, the heterocycle being linked by a carbon atom;

said process comprising:

(A) a first step according to reaction Scheme 1:

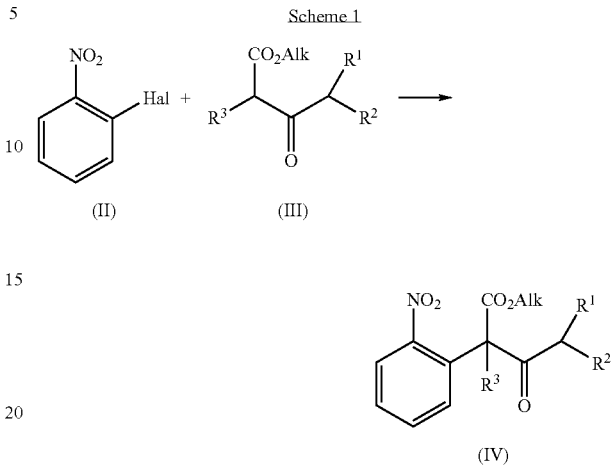

in which:
$R^1$ and $R^2$ are as defined above; and
$R^3$ represents a hydrogen atom or a methyl group;
Hal represents a halogen atom; and
Alk represents a $C_1$-$C_{10}$ alkyl group;
comprising the reaction of a nitrobenzene derivative of general formula (II) with a ketoester derivative of general formula (III), in a compound (III)/compound (II) molar ratio of from 1 to 10, in a solvent and in the presence of a base, the base/compound (I) molar ratio being of from 0.5 to 5;
to provide a nitrophenyl ketoester derivative of general formula (IV);

(B) a second step according to reaction Scheme 2:

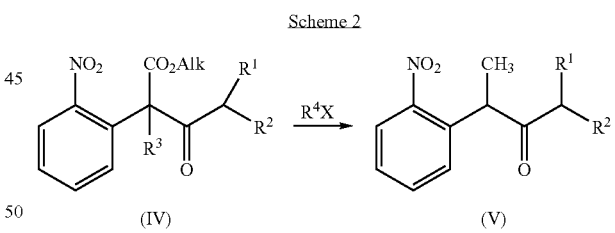

in which:
$R^1$ and $R^2$ are as defined above; and
$R^3$ represents a hydrogen atom or a methyl group;
Alk represents a $C_1$-$C_{10}$ alkyl group;
$R^4$ represents a hydrogen atom or a metal specie; and
X represents a halogen atom;
comprising:
a) in the case $R^3$ is a methyl group, the decarboxylation reaction of a nitrophenyl ketoester derivative of formula (IV) obtained in step one in the presence of an agent $R^4X$, in a ($R^4X$)/compound (IV) molar ratio of from 0.1 to 50; in a solvent and at a temperature of from 20° C. to 180° C.; or b) in the case $R^3$ is a hydrogen atom,
1/the decarboxylation of a nitrophenyl ketoester derivative of formula (IV) obtained in step one in the presence of an agent $R^4X$, in a ($R^4X$)/compound (III) molar ratio of from 0.1 to 50; in a solvent and at a temperature of from 20° C. to 180° C.;
which is then completed by the methylation of the intermediate of general formula (V') previously obtained

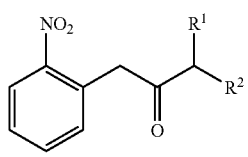

(V')

by adding methylating agent, in a methylating agent/ compound (V') molar ratio of from 0.5 to 2; in a solvent and in the presence of a base, in a base/ compound (V') molar ratio of from 0.5 to 2;
to provide a nitrophenyl ketone derivative of general formula (V);
or
2/the methylation of a nitrophenyl ketoester derivative of formula (IV) obtained in step one by adding methylating agent, in a methylating agent/compound (IV) molar ratio of from 0.5 to 2; in a solvent and in the presence of a base, in a base/compound (IV) molar ratio of from 0.5 to 2;
which is then completed by the decarboxylation of the intermediate of general formula (V") previously obtained

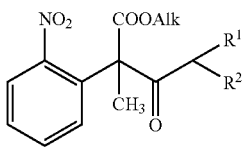

(V")

in the presence of an agent $R^4X$, in a ($R^4X$)/compound (V") molar ratio of from 0.1 to 50; in a solvent and at a temperature of from 20° C. to 180° C.;
to provide a nitrophenyl ketone derivative of general formula (V);
(C) a third step according to reaction Scheme 3:

Scheme 3

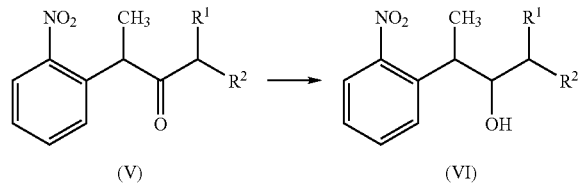

in which $R^1$ and $R^2$ are as defined above;
comprising the reduction of a nitrophenyl ketone of general formula (V) obtained in step two by adding to it from 0.5 to 10 molar equivalent of a reduction agent, in a polar protic solvent and at a temperature of from −20° C. to 80° C.;
to provide a nitrophenyl alcohol derivative of general formula (VI);
(D) a fourth step according to reaction Scheme 4:

Scheme 4

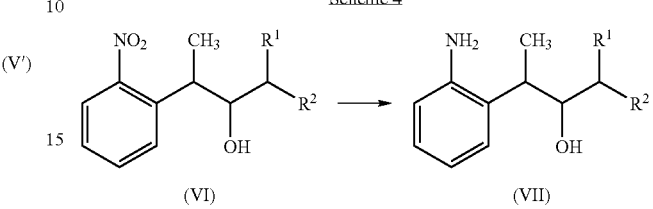

in which $R^1$ and $R^2$ are as defined above;
comprising the reduction by $H_2$ of a nitrophenyl alcohol of general formula (VI) obtained in step three in the presence of a metal catalyst, in a solvent and under a pressure of from 1 to 10 bar;
to provide an aminophenyl alcohol derivative of general formula (VII);
(E) a fifth step according to reaction Scheme 5:

Scheme 5

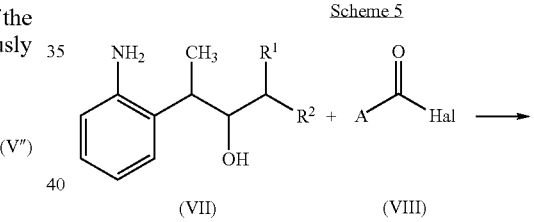

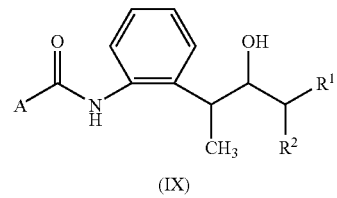

(IX)

in which:
A, $R^1$ and $R^2$ are as defined above; and
Hal represents a halogen atom;
comprising the coupling reaction of an aminophenyl alcohol derivative of general formula (VII) obtained in step four with an acyl halide derivative of general formula (VII), in a solvent and in the presence of a base in a base/compound (VII) molar ratio of 0.5 to 3;
to provide a hydroxycarboxamide derivative of general formula (IX);

(F) a sixth step according to reaction Scheme 6:

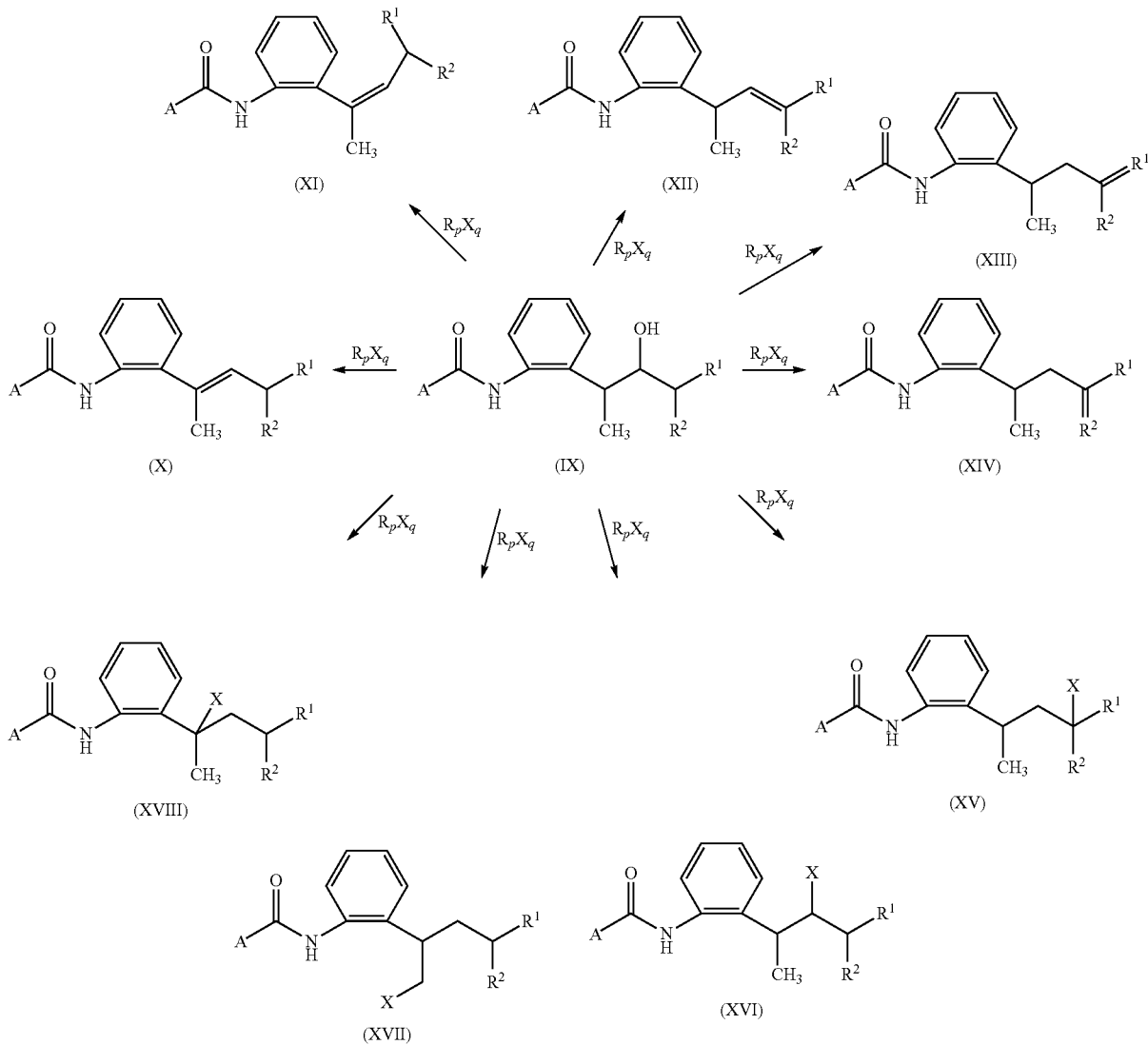

in which:

A, $R^1$ and $R^2$ are as defined above;

p and q are independently chosen as being 1, 2 or 3;

R represents a phosphorous atom, —P═O, —S═O, a mesyl group or a tosyl group;

X represents a halogen atom;

comprising the reaction of a hydroxycarboxamide derivative of general formula (IX) obtained in step five with a compound of formula $R_pX_q$ at a temperature of from 0° C. to 100° C.;

to provide a carboxamide derivative of general formula (X), (XI), (XII), (XIII), (XIV), (XV), (XVI), (XVII) or (XVIII), or a mixture thereof;

(G) a seventh step according to reaction Scheme 7:

Scheme 7

Mixture of carboxamide derivatives of formula (X) to (XVIII) —Reduction→

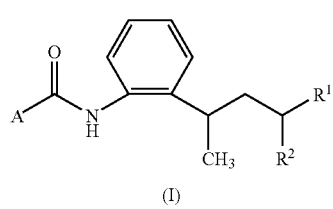

in which A, $R^1$ and $R^2$ are as defined above;

comprising the reduction by $H_2$ of all carboxamide derivatives of general formula (X) to (XVIII) obtained in step six, in the presence of a metal catalyst, in a solvent, at a temperature of from 10° C. to 250° C. and under a pressure of from 1 to 50 Bar;

to provide a carboxamide derivative of general formula (I).

For the purposes of the present invention:

a halogen atom may be a bromine atom, a chlorine atom, an iodine atom or a fluorine atom; preferably, halogen atom means chlorine atom;

carboxy means —C(=O)OH; carbonyl means —C(=O)—; carbamoyl means —C(=O)$NH_2$; —an alkyl group as well as moieties containing this term, can be linear or branched;

a heteroatom may be a sulphur, a nitrogen or an oxygen atom; and a "metal specie" means alkali metal or alkaline earth metal. Preferably, a "metal specie" means a specie chosen from Li, Na or K;

DMA means dimethylacetamide;

DME means 1,2-dimethoxyethane;

DMF means dimethylformamide;

DMSO means dimethyl sulfoxide;

MTBE means methyl tert-butyl ether;

NMP means 1-methyl-2-pyrrolidinone; and

THF means tetrahydrofuran.

Process according to the present invention allows production of a compound of formula (I) starting from a nitro derivative in good yields. This process can be used at an industrial scale.

According to the present invention, substituent $R^1$ of the compound of general formula (I) is defined as being a methyl group, an ethyl group or a $C_1$-$C_4$-haloalkyl group substituted with 1 to 9 halogen atoms chosen from fluorine, chlorine and bromine. Preferably, $R^1$ is chosen as being methyl, ethyl, trifluoromethyl, difluoromethyl, fluoromethyl, trichloromethyl, dichloromethyl, chloromethyl, chlorofluoromethyl, fluorodichloromethyl, difluorochloromethyl, pentafluoroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2-chloro-2,2-difluoroethyl, 2,2-dichloro-2-fluoroethyl, 2,2,2-trichloroethyl, 1-chlorobutyl, heptafluoro-n-propyl or heptafluoroisopropyl. More preferably, $R^1$ is chosen as being methyl, ethyl or trifluoromethyl.

According to the present invention, substituent $R^2$ of the compound of general formula (I) is defined as being a halogen atom, a $C_1$-$C_4$-alkyl group or a $C_1$-$C_4$-haloalkyl group substituted with 1 to 9 halogen atoms chosen from fluorine, chlorine and bromine. Preferably, $R^2$ is chosen as being methyl, ethyl, fluorine, chlorine, bromine, trifluoromethyl, difluoromethyl, fluoromethyl, trichloromethyl, dichloromethyl, chloromethyl, chlorofluoromethyl, fluorodichloromethyl, difluorochloromethyl, pentafluoroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2-chloro-2,2-difluoroethyl, 2,2-dichloro-2-fluoroethyl, 2,2,2-trichloroethyl, 1-chlorobutyl, heptafluoro-n-propyl or heptafluoroisopropyl. More preferably, $R^2$ is chosen as being methyl, ethyl, chlorine or trifluoromethyl.

According to the present invention, the "A" group of the compound of general formula (I) may be a five, six or seven membered ring non-fused heterocycle. Preferably:

* A represents a heterocycle of general formula (A1)

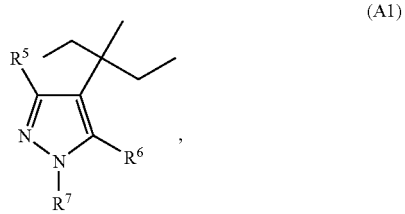

(A1)

in which:

$R^5$ represents hydrogen, cyano, halogen, nitro, $C_1$-$C_4$-alkyl, $C_1$-$C_4$-alkoxy, $C_1$-$C_4$-alkylthio, $C_3$-$C_6$-cycloalkyl, $C_1$-$C_4$-halogenoalkyl, $C_1$-$C_4$-halogenoalkoxy or $C_1$-$C_4$-halogenoalkylthio having in each case 1 to 5 halogen atoms, aminocarbonyl or aminocarbonyl-$C_1$-$C_4$-alkyl;

$R^6$ represents hydrogen, halogen, cyano, $C_1$-$C_4$-alkyl, $C_1$-$C_4$-alkoxy or $C_1$-$C_4$-alkylthio;

$R^7$ represents hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl, $C_1$-$C_4$-halogenoalkyl, $C_1$-$C_4$-halogenoalkylthio-$C_1$-$C_4$-alkyl, $C_1$-$C_4$-halogenoalkoxy-$C_1$-$C_4$-alkyl having in each case 1 to 5 halogen atoms, or phenyl;

or

* A represents a heterocycle of general formula (A2)

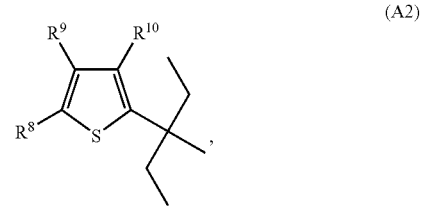

(A2)

in which:

$R^8$ and $R^9$ independently each represents hydrogen, halogen, $C_1$-$C_4$-alkyl or $C_1$-$C_4$-halogenoalkyl having 1 to 5 halogen atoms;

$R^{10}$ represents halogen, cyano or $C_1$-$C_4$-alkyl, or $C_1$-$C_4$-halogenoalkyl or $C_1$-$C_4$-halogenoalkoxy having in each case 1 to 5 halogen atoms;

or

* A represents a heterocycle of general formula (A3)

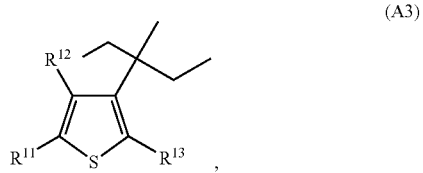

(A3)

in which:

$R^{11}$ and $R^{12}$ independently each represents hydrogen, halogen, $C_1$-$C_4$-alkyl or $C_1$-$C_4$-halogenoalkyl having 1 to 5 halogen atoms;

$R^{13}$ represents hydrogen, halogen, $C_1$-$C_4$-alkyl or $C_1$-$C_4$-halogenoalkyl having 1 to 5 halogen atoms;

or
* A represents a heterocycle of general formula (A4)

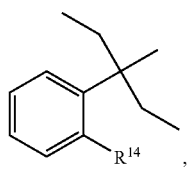
(A4)

in which:
$R^{14}$ represents hydrogen, halogen, hydroxy, cyano, $C_1$-$C_6$-alkyl, $C_1$-$C_4$-halogenoalkyl, $C_1$-$C_4$-halogenoalkoxy or $C_1$-$C_4$-halogenoalkylthio having in each case 1 to 5 halogen atoms;

or
* A represents a heterocycle of general formula (A5)

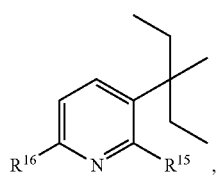
(A5)

in which:
$R^{15}$ represents halogen, hydroxy, cyano, $C_1$-$C_4$-alkyl, $C_1$-$C_4$-alkoxy, $C_1$-$C_4$-alkylthio, $C_1$-$C_4$-halogenoalkyl, $C_1$-$C_4$-halogenoalkylthio or $C_1$-$C_4$-halogenoalkoxy having in each case 1 to 5 halogen atoms;
$R^{16}$ represents hydrogen, halogen, cyano, $C_1$-$C_4$-alkyl, $C_1$-$C_4$-alkoxy, $C_1$-$C_4$-alkylthio, $C_1$-$C_4$-halogenoalkyl, $C_1$-$C_4$-halogenoalkoxy having in each case 1 to 5 halogen atoms, $C_1$-$C_4$-alkylsulphinyl or $C_1$-$C_4$-alkylsulphonyl;

or
* A represents a heterocycle of general formula (A6)

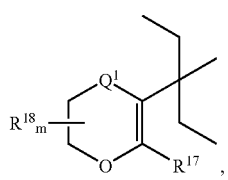
(A6)

in which:
$R^{17}$ represents $C_1$-$C_4$-alkyl or $C_1$-$C_4$-halogenoalkyl having 1 to 5 halogen atoms;
$R^{18}$ represents $C_1$-$C_4$-alkyl,
$Q^1$ represents S (sulphur), SO, $SO_2$ or $CH_2$;
m represents 0, 1 or 2, where $R^{16}$ represents identical or different radicals, when p represents 2;

or
* A represents a heterocycle of general formula (A7)

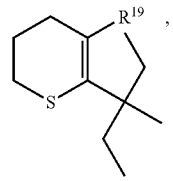
(A7)

in which:
$R^{19}$ represents $C_1$-$C_4$-alkyl or $C_1$-$C_4$-halogenoalkyl having 1 to 5 halogen atoms;

or
* A represents a heterocycle of general formula (A8)

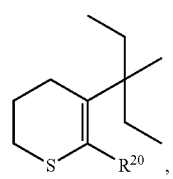
(A8)

in which:
$R^{20}$ represents $C_1$-$C_4$-alkyl or $C_1$-$C_4$-halogenoalkyl having 1 to 5 halogen atoms;

or
* A represents a heterocycle of general formula (A9)

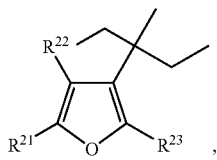
(A9)

in which:
$R^{21}$ and $R^{22}$ independently each represents hydrogen, halogen, amino, $C_1$-$C_4$-alkyl or $C_1$-$C_4$-halogenoalkyl having 1 to 5 halogen atoms;
$R^{23}$ represents hydrogen, halogen, $C_1$-$C_4$-alkyl or $C_1$-$C_4$-halogenoalkyl having 1 to 5 halogen atoms;

or
* A represents a heterocycle of general formula (A 10)

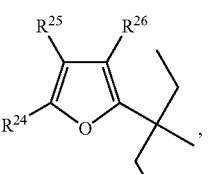
(A10)

in which:
    $R^{24}$ and $R^{25}$ independently each represents hydrogen, halogen, amino, nitro, $C_1$-$C_4$-alkyl or $C_1$-$C_4$-halogenoalkyl having 1 to 5 halogen atoms;
    $R^{26}$ represents hydrogen, halogen, $C_1$-$C_4$-alkyl or $C_1$-$C_4$-halogenoalkyl having 1 to 5 halogen atoms;

or
* A represents a heterocycle of general formula (A1)

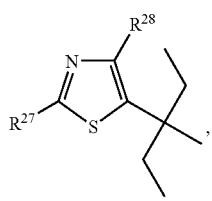
(A11)

in which:
    $R^{27}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-halogenoalkyl having 1 to 5 halogen atoms;
    $R^{28}$ represents halogen, $C_1$-$C_4$-alkyl or $C_1$-$C_4$-halogenoalkyl having 1 to 5 halogen atoms;

or
* A represents a heterocycle of general formula (A12)

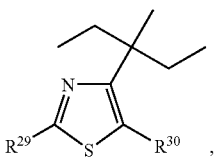
(A12)

in which
    $R^{29}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-halogenoalkyl having 1 to 5 halogen atoms;
    $R^{30}$ represents halogen, $C_1$-$C_4$-alkyl or $C_1$-$C_4$-halogenoalkyl having 1 to 5 halogen atoms;

or
* A represents a heterocycle of general formula (A13)

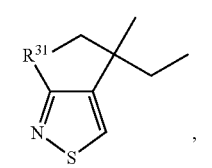
(A13)

in which
    $R^{31}$ represents halogen, $C_1$-$C_4$-alkyl or $C_1$-$C_4$-halogenoalkyl having 1 to 5 halogen atoms;

or
* A represents a heterocycle of general formula (A14)

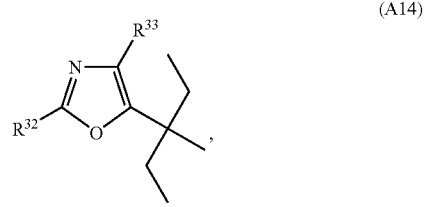
(A14)

in which:
    $R^{32}$ represents hydrogen or $C_1$-$C_4$-alkyl;
    $R^{33}$ represents halogen or $C_1$-$C_4$-alkyl;

or
* A represents a heterocycle of general formula (A15)

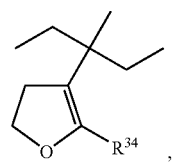
(A15)

in which:
    $R^{34}$ represents $C_1$-$C_4$-alkyl or $C_1$-$C_4$-halogenoalkyl having 1 to 5 halogen atoms;

or
* A represents a heterocycle of general formula (A16)

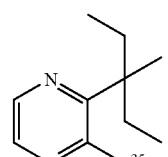
(A16)

in which:
    $R^{35}$ represents hydrogen, halogen, $C_1$-$C_4$-alkyl or $C_1$-$C_4$-halogenoalkyl having 1 to 5 halogen atoms;

or
* A represents a heterocycle of general formula (A17)

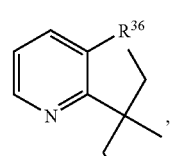
(A17)

in which:
    $R^{36}$ represents halogen, hydroxy, $C_1$-$C_4$-alkyl, $C_1$-$C_4$-alkoxy, $C_1$-$C_4$-alkylthio, $C_1$-$C_4$-halogenoalkyl, $C_1$-$C_4$-halogenoalkylthio or $C_1$-$C_4$-halogenoalkoxy having in each case 1 to 5 halogen atoms;

or
* A represents a heterocycle of general formula (A18)

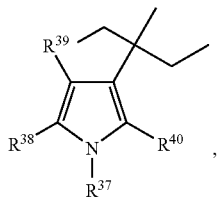
(A18)

in which:
R$^{37}$ represents hydrogen, cyano, C$_1$-C$_4$-alkyl, C$_1$-C$_4$-halogenoalkyl having 1 to 5 halogen atoms, C$_1$-C$_4$-alkoxy-C$_1$-C$_4$-alkyl, hydroxy-C$_1$-C$_4$-alkyl, C$_1$-C$_4$-alkylsulfonyl, di(C$_1$-C$_4$-alkyl)aminosulfonyl, C$_1$-C$_6$-alkylcarbonyl or in each case optionally substituted phenylsulfonyl or benzoyl;
R$^{38}$ represents hydrogen, halogen, C$_1$-C$_4$-alkyl or C$_1$-C$_4$-halogenoalkyl having 1 to 5 halogen atoms;
R$^{39}$ represents hydrogen, halogen, cyano, C$_1$-C$_4$-alkyl or C$_1$-C$_4$-halogenoalkyl having 1 to 5 halogen atoms;
R$^{40}$ represents hydrogen, halogen, C$_1$-C$_4$-alkyl or C$_1$-C$_4$-halogenoalkyl having 1 to 5 halogen atoms;

or
* A represents a heterocycle of general formula (A19)

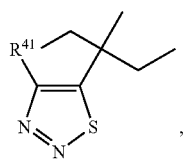
(A19)

in which:
R$^{4'''}$ represents C$_1$-C$_4$-alkyl.

More preferably, A represents a heterocycle of general formula (A1).

The first step (step A) of the process according to the present invention comprises the reaction of a nitrobenzene derivative of general formula (II) with a carbonyl ester derivative of general formula (III), in a compound (II)/compound (II) molar ratio of from 1 to 10, in a solvent and in the presence of a base, the base/compound (II) molar ratio being of from 0.5 to 5 to provide a nitrophenyl ketoester derivative of general formula (IV). Preferably, step A may be conducted in the following conditions, chosen alone or in combination:
the compound (III)/compound (II) molar ratio is of from 1 to 5. More preferably, the compound (III)/compound (II) molar ratio is of from 1 to 2;
the solvent is a polar solvent. Suitable polar solvent includes DMSO, DMF, NMP, DMA, acetonitrile and propionitrile. More preferably, the solvent is DMSO or DMA.
the base is chosen as being hydride, alcolate or carbonate. Suitable hydrides includes NaH and KH. Suitable alcolate includes tBuOK, MeONa and EtON. Suitable carbonate includes K$_2$CO$_3$. More preferably, the base is K$_2$CO$_3$;
the base/compound (II) molar ratio is of from 1 to 3. More preferably, the base/compound (II) molar ratio is of 2.

Step A does not necessarily require specific temperature conditions. Preferably, step A is conducted at a temperature of from 0° C. to 140° C. More preferably, step A is conducted at a temperature of from 10° C. to 100° C. Even more preferably, step A is conducted at a temperature of from 20° C. to 80° C.

Step A does not necessarily require the use of a phase transfer agent. Preferably, step A is conducted in the presence of a phase transfer agent. Suitable phase transfer agent includes a halogeno ammonium salt such as tetraalkylammonium halide.

The second step (step B) of the process according to the present invention comprises a decarboxylation reaction of a nitrophenyl ketoester derivative of formula (IV) obtained in step one or of an intermediate compound of formula (V''') in the presence of an agent R$^4$X, in a (R$^4$X)/compound (IV) or (V''') molar ratio of from 0.1 to 50; in a solvent and at a temperature of from 20° C. to 180° C. to provide a nitrophenyl ketone derivative of general formula (V). Preferably, the decarboxylation reaction may be conducted in the following conditions, chosen alone or in combination:
R$^4$X is chosen as being LiCl or HBr;
the (R$^4$X)/compound (IV) or (V''') molar ratio is of from 0.5 to 30. More preferably, the (R$^4$X)/compound (IV) molar ratio is of from 1 to 20.
the solvent is a polar solvent. Suitable polar solvent includes AcOH, DMF, DMA, NMP and DMSO. More preferably, the solvent is wet polar aprotic when R$^4$X is LiCl and is AcOH when R$^4$X is HBr. More preferably, the solvent is wet DMSO or wet DMF when R$^4$X is LiCl and is AcOH when R$^4$X is HBr;
the reaction is conducted at a temperature of from 100° C. to 160° C. More preferably, the reaction is conducted at a temperature of form 110° C. to 150° C.

The second step (step B) of the process according to the present invention may also comprise a methylation reaction of a compound of formula (IV) or an intermediate compound of formula (V') by adding methylating agent, in a methylating agent/compound (IV) or (V') molar ratio of from 0.5 to 2; in a solvent and in the presence of a base, in a base/compound (IV) or (V') molar ratio of from 0.5 to 2; to provide a nitrophenyl ketone derivative of general formula (V). Preferably, the methylation reaction may be conducted in the following conditions, chosen alone or in combination:
the methylating agent is a haloalkyl group or an alkylsulfate group. More preferably, the methylating agent is MeI or Me$_2$SO$_4$;
the methylating agent/compound (IV) or (V') molar ratio is of from 0.9 to 1.2;
the base is chosen as being NaH, tBuOK, K$_2$CO$_3$, Na$_2$CO$_3$. More preferably, the base is NaH or K$_2$CO$_3$;
the solvent is chosen as being hexane, diethylether, MTBE, THF, dioxane, ethyl acetate or a polar solvent. Suitable polar solvent includes acetone, acetonitrile, NMP, DMF, DMA and DMSO. More preferably, the solvent is a polar solvent.

The third step (step C) of the process according to the present invention comprises the reduction of a nitrophenyl ketone of general formula (V) obtained in step two by adding to it from 0.5 to 10 molar equivalent of a reduction agent, in a polar protic solvent and at a temperature of from −20° C. to 80° C. to provide a nitrophenyl alcohol derivative of general formula (VI). Preferably, step C may be conducted in the following conditions, chosen alone or in combination:
the reduction agent is chosen as being BH$_3$ or RBH4 in which R is chosen from Li, Na or K. More preferably, the reduction agent is NaBH;

the polar protic solvent is an alcohol. More preferably, the polar protic solvent is chosen as being MeOH or EtOH;

the reaction is conducted at a temperature of from −110° C. to 20° C. More preferably, the reaction is conducted at a temperature of 0° C.

The fourth step (step D) of the process according to the present invention comprises the reduction by $H_2$ of a nitrophenyl alcohol derivative of general formula (VI) obtained in step three in the presence of a metal catalyst, in a solvent and under a pressure of from 1 to 10 Bar to provide an aminophenyl alcohol derivative derivative of general formula (VII). Preferably, step D may be conducted in the following conditions, chosen alone or in combination:

the catalyst is chosen as being palladium on charcoal (Pd—C), Raney-nickel or platinum (IV) oxide. More preferably, the catalyst is chosen as being Pd—C;

the solvent is a polar protic solvent. More preferably, the solvent is an alcohol. Suitable alcohol solvent includes methanol and ethanol;

the reaction is conducted under a pressure of from 2 to 5 Bar. More preferably the reaction is conducted under a pressure of 4 Bar.

The fifth step (step E) of the process according to the present invention comprises the coupling reaction of an aminophenyl alcohol derivative of general formula (VII) obtained in step four with an acyl halide derivative of general formula (VIII), in a solvent and in the presence of a base in a base/compound (VII) molar ratio of 0.5 to 3 to provide a hydroxyl carboxamide derivative of general formula (IX). Preferably, step E may be conducted in the following conditions, chosen alone or in combination:

the base is chosen as being pyridine, triethylamine, trimethylamine, sodium carbonate, potassium carbonate, potassium or sodium bicarbonate, sodium hydroxide or potassium hydroxide. More preferably, the base is pyridine or triethylamine;

the base/compound (VII) molar ratio is of 1;

the solvent is chosen as being dichloroethane, dichloromethane, acetonitrile or toluene.

The sixth step (step F) of the process according to the present invention comprises comprising the reaction of a hydroxyl carboxamide derivative of general formula (IX) obtained in step five with a compound of formula $R_pX_q$ at a temperature of from 0° C. to 100° C.;

to provide a carboxamide derivative of general formula (X), (XI), (XII), (XIV), (XV), (XVI), (XVII) or (XVIII) or a mixture thereof;

Preferably, step F may be conducted in the following conditions, chosen alone or in combination:

X is a chlorine atom;

$R_pX_q$ is chosen as being phosphorus oxychloride, thionyl chloride, phosphorous trichloride, phosphorus pentachloride, mesylchloride, tosyl chloride, succinimide or phthalimide chloride;

the reaction is conducted at a temperature of from 0° C. to 80° C.

The step F is not necessarily conducted in the presence of a solvent. Preferably, the step F is conducted in the presence of a solvent. Suitable solvent includes dichloromethane, dichloroethane, toluene, pyridine, DMF, DMA, NMP, DMSO. More preferably the solvent is pyridine;

The step F is not necessarily conducted in the presence of an acid. Preferably the step F is conducted in the presence of an acid. Suitable acid includes phosphoric acid.

The seventh step (step G) of the process according to the present invention comprising the reduction by $H_2$ of all carboxamide derivatives of general formula (X) to (XVII) obtained in step six, in the presence of a metal catalyst, in a solvent, at a temperature of from 10° C. to 250° C. and under a pressure of from 1 to 50 Bar;

to provide a carboxamide derivative of general formula (I). Preferably, step G may be conducted in the following conditions, chosen alone or in combination:

the metal catalyst is chosen as being palladium on charcoal (Pd/C), Raney nickel, $PdCl_2$ or $NiCl_2$;

the solvent is a protic solvent. Suitable protic solvent includes $C_1$-$C_{10}$ alcohol and acetic acid. More preferably, the solvent is octanol;

the reaction is conducted at a temperature of from 40° C. to 200° C.;

the reaction is conducted under a pressure of from 1 to 30 Bar.

The compound of general formula (I) according to the present invention can be prepared according to the above described process. It will nevertheless be understood that, on the basis of his general knowledge and of available publications, the skilled worker will be able to adapt this method according to the specifics of each of the compounds, which it is desired to synthesise.

Certain of the intermediates used for the preparation of compound of general formula (I) are novel. Therefore, the present invention also relates to novel intermediate compounds useful for the preparation of compound of general formula (I). Thus, according to the present invention, there is provided a compound of general formula (IV)

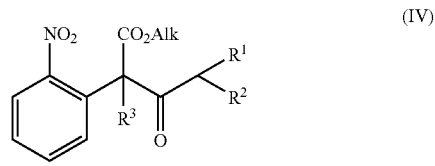

in which:

$R^1$, $R^2$, $R^3$ are as defined above; and

Alk represents a $C_1$-$C_{10}$ alkyl group.

According to the present invention, there is also provided a compound of general formula (V), a compound of general formula (V') and a compound of general formula (V")

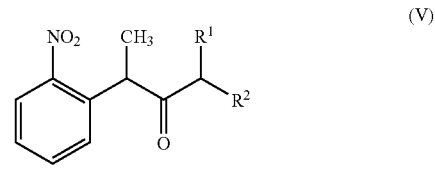

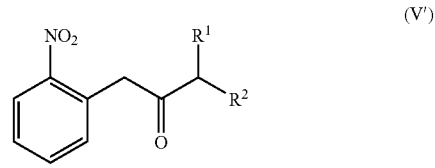

-continued

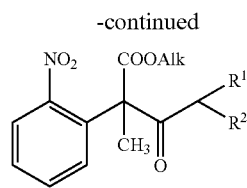
(V″)

in which:
R¹ and R² are as defined above; and
Alk represents a $C_1$-$C_{10}$ alkyl group.

According to the present invention, there is also provided a compound of formula (VI)

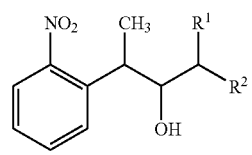
(VI)

in which R¹ and R² are as defined above.

According to the present invention, there is also provided a compound of formula (VII)

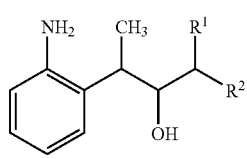
(VII)

in which R¹ and R² are as defined above.

According to the present invention, there is also provided a compound of formula (IX)

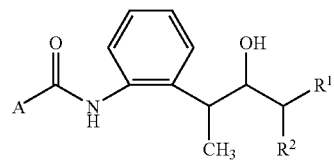
(IX)

in which A, R¹ and R² are as defined above.

According to the present invention, there are also provided compounds of formula (X) to (XVIII)

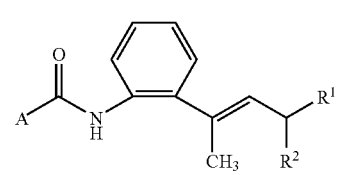
(X)

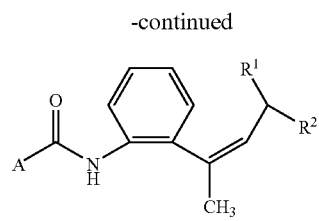
(XI)

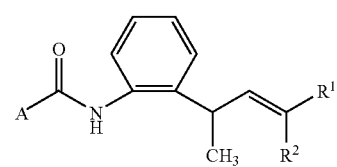
(XII)

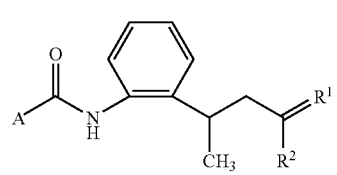
(XIII)

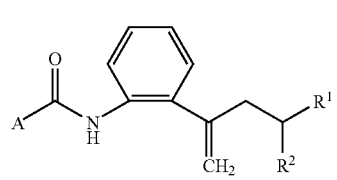
(XIV)

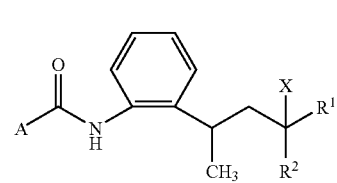
(XV)

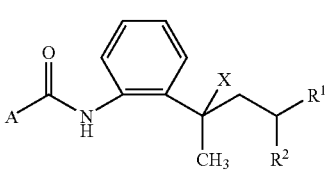
(XVI)

(XVII)

(XVIII)

in which A, X, R¹ and R² are as defined above.

The present invention will now be illustrated with reference to the following examples.

Preparation of 5-fluoro-1,3-dimethyl-N-[2-(1,3-dimethyl)-butyl]-1H-pyrazole-4-carboxamide Step 1: Preparation of 2-(2-nitro-phenyl)-3-oxy-4-methyl-pentanoic acid methyl ester To a solution of fluoronitrobenzene (10 g, 71 mmol) in DMSO (50 ml) were added methylisobutyrylacetate (11.4 ml, 71 mmol) and potassium carbonate (19 g, 138 mmol). The reaction mixture was stirred at 20° C. for 25 hours. It was then cooled to 0° C. and water (50 ml), then aqueous HCl were added to reach pH 7. Ethyl acetate was then added (150 ml). The two phases were separated. The aqueous phase was extracted with ethyl acetate (1×50 ml). The combined organic phase were washed two times with water (2×50 ml) and dried on magnesium sulfate. 12.6 g—yield 67%—of the expected product were obtained in a brown oil.

Further purification by column chromatography may be performed in order to obtain a pure sample of the product as a bright yellow oil.

$^1$H NMR (400 MHz, CDCl$_3$, δ ppm): ketone form/enol form 20/80-ketone form: 8.00 (1H, dd, J=8 Hz, J=1 Hz), 7.62 (1H, dt, J=8 Hz, J=1 Hz), 7.49 (1H, dt, J=8 Hz, J=1 Hz), 5.61 (1H, s), 3.75 (3H, s), 2.83 (1H, m), 1.18 (3H, d, J=7 Hz), 1.09 (3H, d, J=7 Hz)-enol form: 13.0 (1H, d, J=1 Hz), 7.97 (1H, dd, J=8 Hz, J=1 Hz), 7.58 (1H, dt, J=8 Hz, J=1 Hz), 7.47 (1H, dt, J=8 Hz, J=1 Hz), 7.27 (1H, dd, J=8 Hz, J=1 Hz), 3.61 (3H, s), 2.28 (1H, m), 1.09 (3H, d, J=7 Hz), 1.00 (3H, d, J=7 Hz).

Step 2: Preparation of 2-methyl-4-(2-nitro-phenyl)-pentan-3-one

Process 1 a) Preparation of 2,4-dimethyl-2-(2-nitro-phenyl)-3-oxypentanoic acid methyl ester To a solution of 2-(2-nitro-phenyl)-3-oxy-4-methyl-pentanoic acid methyl ester (72%, 5 g, 26 mmol) in DMSO (30 ml) under nitrogen was added potassium carbonate (4.34 g, 31 mmol) and methyliodide (2 ml, 31 mmol). The reaction mixture was then stirred at room temperature for two hours. It was diluted with water (50 ml), and extracted with ethyl acetate (100 ml). The organic phase was then washed with water (5×50 ml), brine, and dried with magnesium sulfate. The crude product was then purified by flash chromatography on biotage apparatus. 3.4 g (yield 90%) of 2,4-dimethyl-2-(2-nitrophenyl)-3-oxypentanoic acid methyl ester was collected as a yellow solid. Melting point was 57.4° C.

$^1$H NMR (400 MHz, CDCl$_3$, δ ppm): 8.02 (1H, dd, J=8 Hz, J=1 Hz), 7.59 (1H, dt, J=8 Hz, J=1 Hz), 7.46 (1H, dt, J=8 Hz, J=1 Hz), 7.21 (1H, dd, J=8 Hz, J=1 Hz), 3.67 (3H, s), 3.36 (1H, m), 1.93 (3H, s), 1.08 (3H, d, J=7 Hz), 1.06 (3H, d, J=7 Hz).

b) Preparation of 2-methyl-4-(2-nitro-phenyl)-pentan-3-one

* Method 1

To a solution of 2,4-dimethyl-2-(2-nitro-phenyl)-3-oxy-pentanoic acid methyl ester (92%, 3.4 g, 11 mmol) in DMSO (30 ml) was added LiCl (516 mg, 12 mmol) and water (438 mg, 24 mmol). The reaction mixture was heated at 140° C. (bath temperature 150° C.) for 2 h. The total conversion was evaluated by HPLC. It was diluted with water (50 ml), and extracted with ethyl acetate (100 ml). The organic phase was then washed with water (5×50 ml), brine, and dried on magnesium sulfate. The crude product was then purified by flash chromatography on biotage apparatus. (2-methyl-4-(2-nitrophenyl)-pentan-3-one (1.46 g, isolated yield 59%) was collected as a yellow oil.

$^1$H NMR (400 MHz, CDCl$_3$, δ ppm): 7.85 (1H, dd, J=8 Hz, J=1 Hz), 7.55 (1H, dt, J=8 Hz, J=1 Hz), 7.38 (2H, m, J=8 Hz, J=1 Hz), 4.52 (1H, q, J=7 Hz), 2.68 (1H, m), 1.44 (3H, d, J=7 Hz), 1.08 (3H, d, J=7 Hz), 0.97 (3H, d, J=7 Hz).

* Method 2

A solution of 2,4-dimethyl-2-(2-nitro-phenyl)-3-oxypentanoic acid methyl ester (92%, 1.20 g, 4.1 mmol) in acetic acid (38.6 ml) and aqueous bromhydric acid (47%, 13.6 ml) was quickly heated to reflux (internal temperature 108-110° C.) and stirred for 2 h30. The reaction mixture was cooled to room temperature and then slowly added to a cold (0° C.) solution of aqueous sodium carbonate. Dichloromethane was added (100 ml). The organic phase was washed with water (2×50 ml), aqueous sodium carbonate (50 ml) water (50 ml), brine (50 ml) and dried with MgSO$_4$. Purification by flash chromatography afforded 2-methyl-4-(2-nitro-phenyl)-pentan-3-one (528 mg—yield 60%) as a yellow oil.

$^1$H NMR (400 MHz, CDCl$_3$, α ppm): 7.85 (1H, dd, J=8 Hz, J=1 Hz), 7.55 (1H, dt, J=8 Hz, J=1 Hz), 7.38 (2H, m, J=8 Hz, J=1 Hz), 4.52 (1H, q, J=7 Hz), 2.68 (1H, m), 1.44 (3H, d, J=7 Hz), 1.08 (3H, d, J=7 Hz), 0.97 (3H, d, J=7 Hz).

Process 2 a) Preparation of 2-methyl-1-(2-nitrophenyl)butan-2-one

To a solution of 2-(2-nitro-phenyl)-3-oxy-4-methyl-pentanoic acid methyl ester (77%, 3.70 g, 21 mmol) in acetic acid was added aqueous bromhydric acid (47%, 50 ml). It was quickly heated to reflux (110° C.) and stirred for 1 h. The reaction mixture was cooled to room temperature, diluted with water (100 ml) and extracted with MTBE (2×50 ml). The combined organic layers were washed with water (2×50 ml), aqueous bicarbonate (2×50 ml), water (2×50 ml) and dried with MgSO$_4$. Light compounds were removed by distillation. The expected product was obtained in a black oil. Further purification by column chromatography may be performed in order to obtain a pure sample of the product as a yellow oil.

$^1$H NMR (400 MHz, CDCl$_3$, δ ppm): 8.08 (1H, dd, J=8 Hz, J=1 Hz), 7.55 (1H, dt, J=8 Hz, J=1 Hz), 7.42 (1H, dt, J=8 Hz, J=1 Hz), 7.24 (1H, m), 4.18 (2H, s), 2.80 (1H, m), 1.19 (6H, d, J=7 Hz).

b) Preparation of 2-methyl-4-(2-nitrophenyl)pentan-3-one

The compound thus obtained was diluted in wet. NaH (60%, 1.18 g, 29.4 mmol) was then added. After gas evolution, MeI (1.83 ml, 29.4 mmol) was added and the reaction stirred at room temperature for 2 h. The reaction was quenched by adding water (50 ml). The aqueous phase was extracted with MTBE (2×150 ml). The organic phase was washed with water (2×150 ml) and dried with MgSO$_4$. Filtration through silica afforded pure 2-methyl-4-(2-nitro-phenyl)-pentan-3-one (1.83 g—yield 77%) as a yellow oil.

$^1$H NMR (400 MHz, CDCl$_3$, δ ppm): 7.85 (1H, dd, J=8 Hz, J=1 Hz), 7.55 (1H, dt, J=8 Hz, J=1 Hz), 7.38 (2H, m, J=8 Hz, J=1 Hz), 4.52 (1H, q, J=7 Hz), 2.68 (1H, m), 1.44 (3H, d, J=7 Hz), 1.08 (3H, d, J=7 Hz), 0.97 (3H, d, J=7 Hz).

Step 3: Preparation of
2-methyl-4-(2-nitro-phenyl)-pentan-3-ol

In a 25 ml flask was prepared a solution of 2-methyl-4-(2-nitro-phenyl)-pentan-3-one (390 mg, 1.8 mmol) in dry methanol (9 ml). It is cooled with an ice-water bath. The temperature in the reaction mixture was 4° C. Sodium borohydride (73 mg, 1.9 mmol) was added, spoon by spoon. It was stirred one hour at 0° C. The cooled mixture was added to HCl 1N (7 ml). This addition was exothermic. Methanol was evaporated. The aqueous phase was extracted with ethyl acetate (50 ml). The organic phase was washed with water (1×25 ml), brine (1×25 ml) and dried with magnesium sulfate. 2-methyl-4-(2-nitro-phenyl)-pentan-3-ol (380 mg—yield 97%) was then obtained as a pale yellow oil.

$^1$H NMR (400 MHz, CDCl$_3$, δ ppm): 7.70 (1H, dd, J=8 Hz, J=1 Hz), 7.60 (1H, dd, J=8 Hz, J=1 Hz), 7.56 (1H, ddd, J=8 Hz, J=7 Hz, J=1 Hz), 7.34 (1H, ddd, J=8 Hz, J=7 Hz, J=1 Hz), 3.49 (1H, m), 3.45 (1H, m), 1.90 (1H, m), 1.77 (1H, s), 1.29 (3H, d, J=7 Hz), 0.99 (3H, d, J=7 Hz), 0.92 (3H, d, J=7 Hz).

Step 4: Preparation of
2-methyl-4-(2-amino-phenyl)-pentan-3-ol

In a 15 ml hydrogenation reactor was charged a solution of 2-methyl-4-(2-nitro-phenyl)-pentan-3-ol (370 mg, 1.7 mmol) in EtOH (12 ml). Pd/C$_5$% was added. The reaction mixture was stirred under hydrogen (4 bars) at room temperature for 2 hours. Filtration through celite and evaporation of ethanol afforded 2-methyl-4-(2-amino-phenyl)-pentan-3-ol as a white solid (320 mg-quantitative yield).

$^1$H NMR (400 MHz, CDCl$_3$, δ ppm): 7.14 (1H, dd, J=8 Hz, J=1 Hz), 7.03 (1H, dt, J=8 Hz, J=1 Hz), 6.81 (1H, dt, J=8 Hz, J=1 Hz), 6.69 (1H, dd, J=8 Hz, J=1 Hz), 3.69 (1H, q, J=7 Hz), 3.44 (1H, dd, J=9 Hz, J=3 Hz), 3.02 (1H, m), 1.77 (1H, s), 1.29 (3H, d, J=7 Hz), 0.99 (3H, d, J=7 Hz), 0.92 (3H, d, J=7 Hz).

MS (EI) Found [M+H]$^+$: 194.1537. C$_{12}$H$_{20}$NO requires 194.1545

Step 5: Preparation of 5-fluoro-1,3-dimethyl-N-[2-(1,3-dimethyl-2-hydroxybutyl)-phenyl]-1H-pyrazole-4-carboxamide To a cold (0° C.) solution of 2-methyl-4-(2-amino-phenyl)-pentan-3-ol (230 mg, 1.2 mmol) in toluene (10 ml) were added triethylamine (0.2 ml, 1.4 mmol) and a solution of 1,3-dimethyl-1H-pyrazole-4-carbonyl chloride in toluene (4.75M, 0.3 ml, 1.4 mmol). The reaction was stirred one hour at room temperature. Water (10 ml) was then added. The aqueous phase was washed with dichloromethane. The combined organic phases were washed with HCl 1N (10 ml), water (10 ml) and brine (10 ml), then dried with magnesium sulfate. Washing the solid residue with toluene afforded 5-fluoro-1,3-dimethyl-N-[2-(1,3-dimethyl-2-hydroxybutyl)phenyl]-1H-pyrazole-4-carboxamide (315 mg—yield 79%) as a white solid. Melting point was 117.8° C.

$^1$H NMR (400 MHz, CDCl$_3$, δ ppm): $^1$H NMR (400 MHz, CDCl$_3$, δ ppm): 8.61 (1H, s), 7.66 (1H, dd, J=8 Hz, J=1 Hz), 7.26 (1H, dd, J=8 Hz, J=1 Hz), 7.19 (1H, m), 7.15 (1H, m), 3.65 (3H, d, J=1 Hz), 3.36 (1H, ddd, J=10 Hz, J=4 Hz, J=2 Hz), 3.10 (1H, m), 2.43 (3H, s), 2.33 (1H, d, J=4 Hz), 1.95 (1H, m), 1.19 (3H, d, J=7 Hz), 0.98 (3H, d, J=7 Hz), 0.92 (3H, d, J=7 Hz).

MS (EI) Found [M+Na]$^+$: 356.1742. C$_{18}$H$_{24}$N$_3$O$_2$FNa requires 356.1750

Step 6: Preparation and catalytic reduction of a mixture of 5-fluoro-1,3-dimethyl-N-[2-(1,3-dimethyl)-buten-1-yl]-1H-pyrazole-4-carboxamide, 5-fluoro-1,3-dimethyl-N-[2-(1,3-dimethyl)-buten-2-yl]-1H-pyrazole-4-carboxamide and 5-fluoro-1,3-dimethyl-N-[2-(2-chloro-1,3-dimethyl)-butyl]-1H-pyrazole-4-carboxamide (45:39:16 w)

To a solution of 5-fluoro-1,3-dimethyl-N-[2-(1,3-dimethyl-2-hydroxy)-butyl]-1H-pyrazole-4-carboxamide (307 mg, 0.9 mmol) in pyridine were added H$_3$PO$_4$ (aq. 85%, 0.08 ml) and phosphorous oxychloride (1.52 ml, 16 mmol). The reaction mixture was stirred for 3 h. It was then added onto cooled water and extracted with ethyl acetate. The organic phase was washed with 1N HCl, brine, and dried with MgSO$_4$. The mixture of compounds (280 mg, yield 95%) was obtained as a white solid.

These compounds are fully characterised in mixture (HPLC-MS and $^1$H NMR, $^{13}$C NMR, $^{19}$F NMR).

$^1$H NMR (400 MHz, CDCl$_3$, δ ppm): 5-fluoro-1,3-dimethyl-N-[2-(1,3-dimethylbuten-1-yl)phenyl]-1H-pyrazole-4-carboxamide: 8.42 (1H, d, J=8 Hz), 7.76 (1H, m), 7.27 (1H, m), 7.02 (1H, m), 7.01 (1H, m), 5.53 (1H, d, J=10 Hz), 3.71 (3H, m), 2.45 (3H, s), 2.02 (1H, m), 1.92 (3H, s), 0.84 (6H, m)-5-fluoro-1,3-dimethyl-N-[2-(1,3-dimethylbuten-2-yl)phenyl]-1H-pyrazole-4-carboxamide: 7.72 (1H, dd, J=8 Hz, J=1 Hz), 7.45 (1H, s), 7.20-7.14 (3H, m), 5.18 (1H, d, J=9 Hz), 3.71 (4H, m), 2.45 (3H, s), 1.70 (3H, s), 1.60 (3H, s), 1.30 (3H, d, J=7 Hz)-5-fluoro-1,3-dimethyl-N-[2-(2-chloro-1,3-dimethylbutyl)phenyl]-1H-pyrazole-4-carboxamide: 7.28-7.02 (4H, m), 4.04 (1H, dd, J=9 Hz, J=1 Hz), 3.71 (3H, m), 3.25 (1H, dq, J=9 Hz, J=1 Hz), 2.47 (3H, m), 1.75 (1H, m), 1.41 (3H, d, J=7 Hz), 0.92 (3H, d, J=7 Hz), 0.87 (3H, d, J=7 Hz).

Step 7: Preparation of 5-fluoro-1,3-dimethyl-N-[2-(1,3-dimethyl)-but-2-ol-yl]-1H-pyrazole-4-carboxamide To the mixture obtained in the above step 6 in octanol, activated 5% Pd/C catalyst was added and stirred at 185° C. in a hydrogen atmosphere (20 bars). Octanol was removed by azeotropic distillation with water. The resulting suspension was dissolved with MTBE. The organic phase was dried with MgSO$_4$. Thus obtained 5-fluoro-1,3-dimethyl-N-[2-(1,3-dimethylbutyl)phenyl]-1H-pyrazole-4-carboxamide as a white solid (95%, 246 mg, yield 81%).

$^1$H NMR (400 MHz, CDCl$_3$, δ ppm): 5-fluoro-1,3-dimethyl-N-[2-(1,3-dimethyl)-butyl]-1H-pyrazole-4-carboxamide: 7.79 (1H, dd, J=8 Hz, J=1 Hz), 7.27 (1H, s), 7.25 (1H, m), 7.18 (1H, m), 7.16 (1H, m), 3.74 (3H, d, J=1 Hz), 2.97 (1H, m), 2.48 (3H, s), 1.54 (2H, m), 1.42 (1H, m), 1.21 (3H, d, J=7 Hz), 0.85 (6H, d, J=6 Hz).

The invention claimed is:
1. A process for the preparation of a carboxamide derivative of formula (I) or a salt thereof

$$\text{(I)}$$

in which:
R$^1$ represents a methyl group, an ethyl group or a C$_1$-C$_4$-haloalkyl group substituted with 1 to 9 halogen atoms chosen from fluorine, chlorine and bromine;
R$^2$ represents a halogen atom, a C$_1$-C$_4$-alkyl group or a C$_1$-C$_4$-haloalkyl group substituted with 1 to 9 halogen atoms chosen from fluorine, chlorine and bromine; and
A represents an optionally substituted 5-, 6- or 7-membered non-fused heterocycle with one, two or three heteroatoms which may be the same or different, the heterocycle being linked by a carbon atom;
said process comprising:
(A) a first step according to reaction Scheme 1:

Scheme 1 in which:
R$^1$ and R$^2$ are as defined above; and
R$^3$ represents a hydrogen atom or a methyl group;
Hal represents a halogen atom; and
Alk represents a C$_i$-C$_i$o alkyl group;
comprising the reaction of a nitrobenzene derivative of formula (II) with a ketoester derivative of formula (III), in a compound (III)/compound (II) molar ratio of from 1 to 10, in a solvent and in the presence of a base, the base/compound (II) molar ratio being of from 0.5 to 5;
to provide a nitrophenyl ketoester derivative of formula (IV);
(B) a second step according to reaction Scheme 2

Scheme 2 in which:
R$^1$ and R$^2$ are as defined above; and
R$^3$ represents a hydrogen atom or a methyl group;
Alk represents a C$_i$-C$_i$o alkyl group;
R$^4$ represents a hydrogen atom or a metal species; and
X represents a halogen atom;
comprising:
(a) in the case R$^3$ is a methyl group, the decarboxylation reaction of a nitrophenyl ketoester derivative of formula (IV) obtained in step one in the presence of an agent R$^4$X, in a (R$^4$X)/compound (IV) molar ratio of from 0.1 to 50; in a solvent and at a temperature of from 20° C. to 180° C.; or
(b) in the case R$^3$ is a hydrogen atom,
1/the decarboxylation of a nitrophenyl ketoester derivative of formula (IV) obtained in step one in the presence of an agent R$^4$X, in a (R$^4$X)/compound (III) molar ratio of from 0.1 to 50; in a solvent and at a temperature of from 20° C. to 180° C.;
which is then completed by the methylation of the intermediate of formula (V') previously obtained $$\text{(V')}$$

by adding methylating agent, in a methylating agent/compound (V') molar ratio of from 0.5 to 2; in a solvent and in the presence of a base, in a base/compound (V') molar ratio of from 0.5 to 2;
to provide a nitrophenyl ketone derivative of formula (V);
or
2/the methylation of a nitrophenyl ketoester derivative of formula (IV) obtained in step one by adding methylating agent, in a methylating agent/compound (IV) molar ratio of from 0.5 to 2; in a solvent and in the presence of a base, in a base/compound (IV) molar ratio of from 0.5 to 2;
which is then completed by the decarboxylation of the intermediate of formula (V") previously obtained $$\text{(V")}$$

in the presence of an agent R$^4$X, in a (R$^4$X)/compound (V") molar ratio of from 0.1 to 50; in a solvent and at a temperature of from 20° C. to 180° C.;
to provide a nitrophenyl ketone derivative of formula (V);

(C) a third step according to reaction Scheme 3:

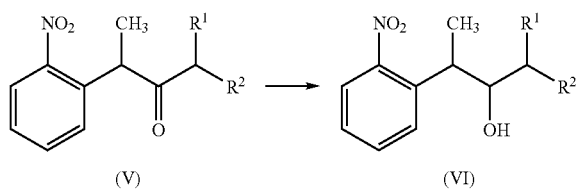

in which R¹ and R² are as defined above;
comprising the reduction of a nitrophenyl ketone of formula (V) obtained in step two by adding to it from 0.5 to 10 molar equivalent of a reduction agent, in a polar protic solvent and at a temperature of from −20° C. to 80° C.;
to provide a nitrophenyl alcohol derivative of formula (VI);
(D) a fourth step according to reaction Scheme 4:

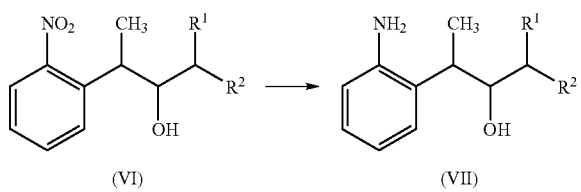

in which R¹ and R² are as defined above;
comprising the reduction by $H_2$ of a nitrophenyl alcohol of formula (VI) obtained in step three in the presence of a metal catalyst, in a solvent and under a pressure of from 1 to 10 bar; to provide an aminophenyl alcohol derivative of formula (VII);
(E) a fifth step according to reaction Scheme 5:

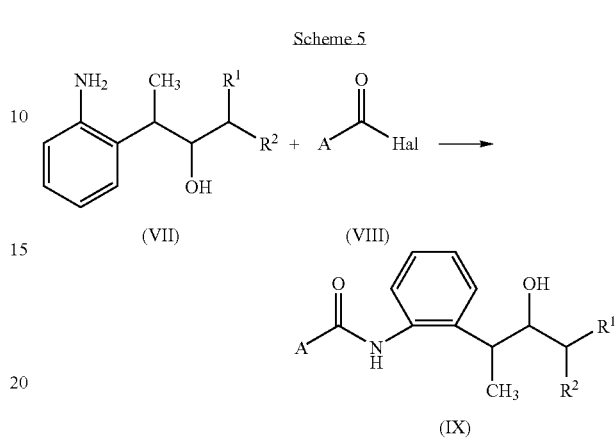

in which:
A, R¹ and R² are as defined above; and
Hal represents a halogen atom;
comprising the coupling reaction of an aminophenyl alcohol derivative of formula (VII) obtained in step four with an acyl halide derivative of formula (VIII), in a solvent and in the presence of a base in a base/compound (VII) molar ratio of 0.5 to 3;
to provide a hydroxycarboxamide derivative of formula (IX);
(F) a sixth step according to reaction Scheme 6:

Scheme 6
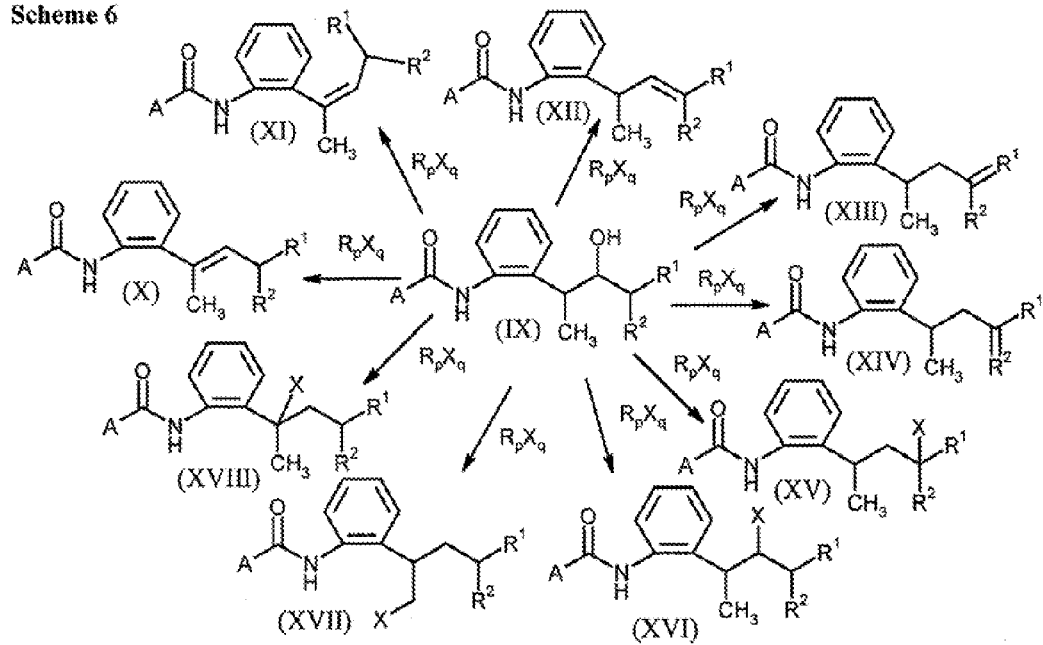

in which:

A, $R^1$ and $R^2$ are as defined above;

p and q are independently chosen as being 1, 2 or 3;

R represents a phosphorous atom, —P=O, —S=0, a mesyl group or a tosyl group;

X represents a halogen atom;

comprising the reaction of a hydroxycarboxamide derivative of formula (IX) obtained in step five with a compound of formula $R_pX_q$ at a temperature of from 0° C. to 100° C.;

to provide a carboxamide derivative of formula (X), (XI), (XII), (XIII), (XIV), (XV), (XVI), (XVII) or (XVIII), or a mixture thereof;

(G) a seventh step according to reaction Scheme 7:

Scheme 7

Mixture of carboxamide derivatives of formula (X) to (XVIII) —Reduction→

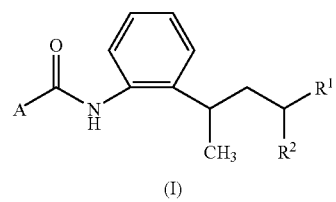

(I)

in which A, $R^1$ and $R^2$ are as defined above;

comprising the reduction by $H_2$ of all carboxamide derivatives of formula (X) to (XVIII) obtained in step six, in the presence of a metal catalyst, in a solvent, at a temperature of from 10° C. to 250° C. and under a pressure of from 1 to 50 Bar;

to provide a carboxamide derivative of formula (I).

2. A process according to claim 1, wherein $R^1$ is methyl, ethyl, trifluoromethyl, difluoromethyl, fluoromethyl, trichloromethyl, dichloromethyl, chloromethyl, chlorofluoromethyl, fluorodichloromethyl, difluorochloromethyl, pentafluoroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2-chloro-2,2-difluoroethyl, 2,2-dichloro-2-fluoroethyl, 2,2,2-trichloroethyl, 1-chlorobutyl, heptafluoro-n-propyl or heptafluoroisopropyl.

3. A process according to claim 1, wherein $R^2$ is methyl, ethyl, fluorine, chlorine, bromine, trifluoromethyl, difluoromethyl, fluoromethyl, trichloromethyl, dichloromethyl, chloromethyl, chlorofluoromethyl, fluorodichloromethyl, difluorochloromethyl, pentafluoroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2-chloro-2,2-difluoroethyl, 2,2-dichloro -2-fluoroethyl, 2,2,2-trichloroethyl, 1-chlorobutyl, heptafluoro-n-propyl or heptafluoroisopropyl.

4. A process according to claim 1, wherein A represents a heterocycle of formula (A1)

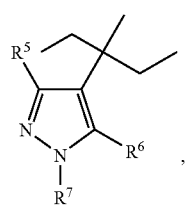

(A1)

in which:

$R^5$ represents hydrogen, cyano, halogen, nitro, $C_1$-$C_4$-alkyl, $C_1$-$C_4$-alkoxy, $C_1$-$C_4$-alkylthio, $C_3$-$C_6$-cycloalkyl, $C_1$-$C_4$-halogenoalkyl, $C_1$-$C_4$-halogenoalkoxy or $C_1$-$C_4$-halogenoalkylthio having in each case 1 to 5 halogen atoms, aminocarbonyl or aminocarbonyl-$C_1$-$C_4$-alkyl;

$R^6$ represents hydrogen, halogen, cyano, $C_1$-$C_4$-alkoxy or $C_1$-$C_4$-alkylthio; and $R^7$ represents hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl, $C_1$-$C_4$-halogenoalkyl, $C_1$-$C_4$-halogenoalkylthio-$C_1$-$C_4$-alkyl, $C_1$-$C_4$-halogenoalkoxy-$C_1$-$C_4$-alkyl having in each case 1 to 5 halogen atoms, or phenyl.

5. A process according to claim 1 wherein step A is conducted at a temperature of from 0° C. to 140° C.

6. A process according to claim 1 wherein step A is conducted in the presence of a phase transfer agent.

7. A process according to claim 1 wherein step F is conducted in the presence of a solvent.

8. A process according to claim 1 wherein step F is conducted in the presence of an acid.

9. A compound of formula (IV)

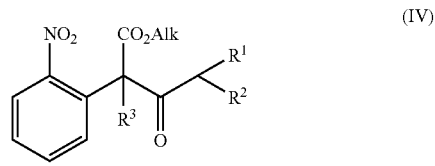

(IV)

wherein $R^1$ is a methyl group, an ethyl group or a $C_1$-$C_4$-haloalkyl group substituted with 1 to 9 halogen atoms chosen from fluorine, chlorine and bromine;

$R^2$ is a halogen atom, a $C_1$-$C_4$-alkyl group or a $C_1$-$C_4$-haloalkyl group substituted with 1 to 9 halogen atoms chosen from fluorine, chlorine and bromine;

R3 is a hydrogen atom or a methyl group; and

ALK represents a $C_1$-$C_{10}$ alkyl group.

10. A compound of formula (V)

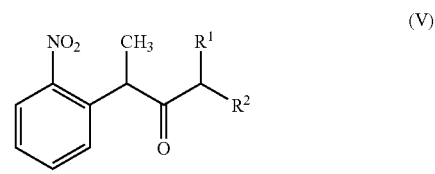

(V)

wherein $R^1$ is a methyl group, an ethyl group or a $C_1$-$C_4$-haloalkyl group substituted with 1 to 9 halogen atoms chosen from fluorine, chlorine and bromine; and $R^2$ is a halogen atom, a $C_1$-$C_4$-alkyl group or a $C_1$-$C_4$-haloalkyl group substituted with 1 to 9 halogen atoms chosen from fluorine, chlorine and bromine.

11. A compound of formula (V″)

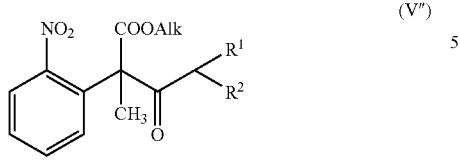

(V″)

wherein
R¹ is a methyl group, an ethyl group or a $C_1$-$C_4$-haloalkyl group substituted with 1 to 9 halogen atoms chosen from fluorine, chlorine and bromine;
R² is a halogen atom, a $C_1$-$C_4$-alkyl group or a $C_1$-$C_4$-haloalkyl group substituted with 1 to 9 halogen atoms chosen from fluorine, chlorine and bromine; and
Alk represents a $C_1$-$C_{10}$ alkyl group.

12. A compound of formula (VI)

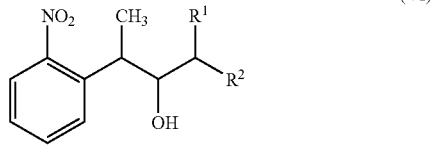

(VI)

wherein
R¹ is a methyl group, an ethyl group or a $C_1$-$C_4$-haloalkyl group substituted with 1 to 9 halogen atoms chosen from fluorine, chlorine and bromine; and
R² is a halogen atom, a $C_1$-$C_4$-alkyl group or a $C_1$-$C_4$-haloalkyl group substituted with 1 to 9 halogen atoms chosen from fluorine, chlorine and bromine.

13. A compound of formula (VII)

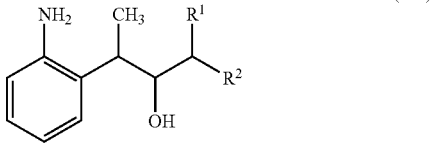

(VII)

wherein
R¹ is a methyl group, an ethyl group or a $C_1$-$C_4$-haloalkyl group substituted with 1 to 9 halogen atoms chosen from fluorine, chlorine and bromine;
R² is a halogen atom, a $C_1$-$C_4$-alkyl group or a $C_1$-$C_4$-haloalkyl group substituted with 1 to 9 halogen atoms chosen from fluorine, chlorine and bromine.

14. A compound of formula (IX)

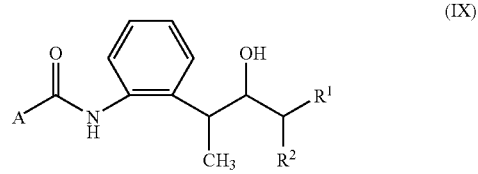

(IX)

wherein
A is an optionally substituted 5-, 6- or 7-membered non-fused heterocycle with one, two or three heteroatoms which may be the same or different, the heterocycle being linked by a carbon atom;
R¹ is a methyl group, an ethyl group or a $C_1$-$C_4$-haloalkyl group substituted with 1 to 9 halogen atoms chosen from fluorine, chlorine and bromine; and
R² is a halogen atom, a $C_1$-$C_4$-alkyl group or a $C_1$-$C_4$-haloalkyl group substituted with 1 to 9 halogen atoms chosen from fluorine, chlorine and bromine.

15. A compound of formula (XII), (XIII), (XV), (XVI), (XVII), or (XVIII)

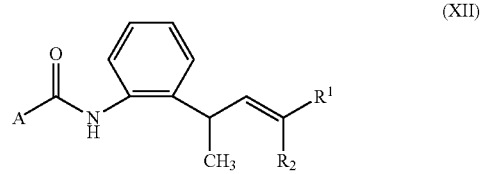

(XII)

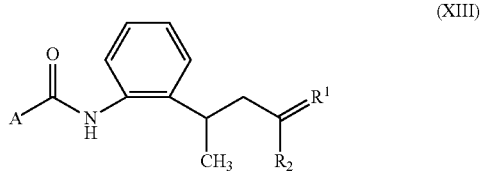

(XIII)

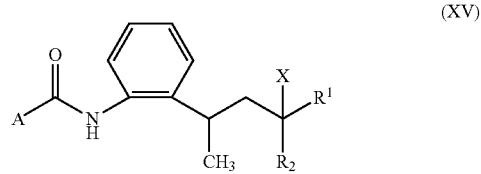

(XV)

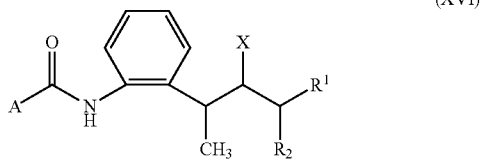

(XVI)

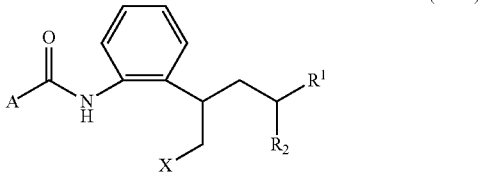

(XVII)

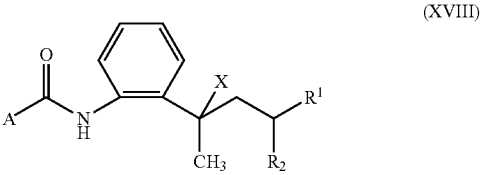

(XVIII)

wherein
A is an optionally substituted 5-, 6- or 7-membered non-fused heterocycle with one, two or three heteroatoms which may be the same or different, the heterocycle being linked by a carbon atom;
X is a halogen atom;
R¹ is a methyl group, an ethyl group or a $C_1$-$C_4$-haloalkyl group substituted with 1 to 9 halogen atoms chosen from fluorine, chlorine and bromine; and $R^2$ is a halogen atom, a $C_1$-$C_4$-alkyl group or a $C_1$-$C_4$-haloalkyl group substituted with 1 to 9 halogen atoms chosen from fluorine, chlorine and bromine.

16. The compound of claim 15, comprising the compound of formula (XII).

17. The compound of claim 15, comprising the compound of formula (XIII).

18. The compound of claim 15, comprising the compound of formula (XV).

19. The compound of claim 15, comprising the compound of formula (XVI).

20. The compound of claim 15, comprising the compound of formula (XVII).

* * * * *